United States Patent [19]

Mack

[11] Patent Number: 4,511,332

[45] Date of Patent: Apr. 16, 1985

[54] DENTAL ARTICULATOR

[76] Inventor: Heinz Mack, Südl. Auffahrtsallee 64, 8000 München 19, Fed. Rep. of Germany

[21] Appl. No.: 521,225

[22] Filed: Aug. 9, 1983

Related U.S. Application Data

[63] Continuation of Ser. No. 293,241, Aug. 17, 1981, abandoned.

[30] Foreign Application Priority Data

Sep. 5, 1980 [DE] Fed. Rep. of Germany ....... 3033390

[51] Int. Cl.³ ............................................. A61C 11/00
[52] U.S. Cl. ........................................ 433/59; 433/54
[58] Field of Search .................................... 433/54–67; 38/79

[56] References Cited

U.S. PATENT DOCUMENTS

| | | | |
|---|---|---|---|
| 1,157,961 | 10/1915 | Reichold | 38/79 |
| 2,608,761 | 9/1952 | Scott | 433/56 |
| 2,816,360 | 12/1957 | Stuart | 433/55 |
| 3,019,530 | 2/1962 | DePietro | 433/59 |
| 3,035,350 | 5/1962 | Franwick | 433/59 |
| 3,092,909 | 6/1963 | Miller | 433/60 |
| 3,159,915 | 12/1964 | Beu et al. | 433/59 |
| 3,160,955 | 12/1964 | DePietro | 433/56 |
| 3,206,852 | 9/1965 | Swanson | 433/56 |
| 3,593,442 | 7/1971 | Davidson et al. | 38/79 |
| 3,965,576 | 6/1976 | Eveland | 433/60 |

FOREIGN PATENT DOCUMENTS 845235 7/1952 Fed. Rep. of Germany ........ 433/55

*Primary Examiner*—John J. Wilson
*Attorney, Agent, or Firm*—Larson and Taylor

[57] ABSTRACT

The invention relates to a dental articulator in which the support table for the front tooth guide pin is disposed on the upper frame part and the adjustable front tooth guide pin is disposed on the lower frame part. The table plate of the support table is preferably divided into two regions, of which one region, which provides the central support, remains invariably in the horizontal position, while the other region, in which the excursions of the front tooth guide pin take place, is pivotable downwards at the front relative to the transverse axis of the articulator and can be locked in any desired inclined position. In addition, the support table is preferably arranged rotatably in the plane of its base surface, in order to be able to determine better the progression of the guide surfaces of the different teeth when a lateral movement is made. On the upper portion of the upper frame part there is preferably disposed a support device which ensures secure support when the articulator is laid down on its back and also when only the upper frame part is laid down on its back.

3 Claims, 17 Drawing Figures

DENTAL ARTICULATOR

This application is a continuation of application Ser. No. 293,241 filed Aug. 17, 1981 and now abandoned.

The present invention relates to a dental articulator consisting essentially of a lower frame part with the holding device for the mounting plate for the lower jaw model, a vertical frame part which is fastened to the lower frame part and has two articulation heads, and an upper frame part with the two radially rotatable articulation sockets, the holding device for the mounting plate for the upper jaw model, an adjustable front tooth guide pin, and a support table for the front tooth guide pin.

Dental articulators of the kind described above are known in the most diverse forms of construction. Thus, for example, in German Patent Specification No. 2,511,388 a dental articulator is described, which consists essentially of a lower frame part with the holding device for the mounting plate for the lower jaw model and a support table for the front tooth guide pin, a vertical frame part which is fastened to the lower frame part and has two balls serving as articulation heads and mounted on two carrier pins, and an upper frame part with the two radially rotatable ball sockets which serve as articulation sockets, and which are provided with a rear ball guide device and an inner ball guide device angularly adjustable relative to the rear ball guide device and also with the bearing shaft, the holding device for the mounting plate for the upper jaw model, and an adjustable front tooth guide pin.

All dental articulators known hitherto have one feature in common, namely the fact that the front tooth guide pin is fastened to the upper frame part and the support table for the front tooth guide pin is fastened to the lower frame part.

According to the invention it has been realised that this arrangement of the front tooth guide pin and support table is extremely disadvantageous, because the front tooth guide surface is reproduced in reciprocal form. In other words, owing to the fact that the front tooth guide pin is not disposed in accordance with the actual movement process, a record exactly opposite to nature is obtained. In addition, it has been found disadvantageous that when the vertical dimension of the front tooth guide pin is changed, a horizontal displacement of the point of impact results. In order to overcome this disadvantage to some extent it was necessary to curve the front tooth guide pin at its free end facing the support table, or to move the support table continuously.

The object of the invention is therefore that of providing a dental articulator exempt from the disadvantages described above.

According to the invention this object has been achieved by disposing the support table for the front tooth guide pin on the upper frame part and the adjustable front tooth guide pin on the lower frame part. It is thereby ensured that equidirectional representation of the front tooth guide surface is achieved and that with a vertical dimension arrangement (adjustment) there will be no noteworthy displacement, that is to say no noteworthy alteration of the point of impact.

The plane of the support table before commencement should preferably lie in the reference plane, since this results in minimum deviations from normal values.

In addition, it has been found advantageous to divide the table plate of the support table into two regions, of which one region, which provides central support, that is to say the region on which the front tooth guide pin rests before commencement of the excursions, remains invariably in the horizontal position, while the other region, in which the excursions of the front tooth guide pin take place, is pivotable downwards at the front relative to the transverse axis of the articulator and can be locked in any desired inclined position. The inclined position to be adjusted in any given case corresponds to the front tooth guide surface of the front teeth on the upper jaw of the bite model to be examined.

It has in addition been found very advantageous to dispose the support table in such a manner that it is rotatable in the plane of its base surface in order to enable the progression of the guide surface of the various teeth to be better determined when a sideways movement (lateral movement) occurs. This can for example be achieved by unlocking the locking screw, which is disposed centrally relative to the support table, turning the support table into the desired position, and then locking it again. It is however more advantageous for the support table to be fastened so as to be centrally rotatable on a base plate. For this purpose the base plate may be centrally joined to the base of the support table, for example by tight-fitting riveting or by a screw/-spring connection, whereby rotation to any desired position is possible without first unlocking and then relocking. In this case the base plate is itself fastened to the articulator part, for example by means of a locking screw. An arrangement is particularly preferred in which the base of the support table is rotatably mounted on the base plate by means of a cylindrical pivot pin which is disposed centrally and projects into the center of the base plate, and in which the base of the support table is pressed by means of a spring-loaded screw/-spring connection, disposed some distance from the center, so firmly against the base plate that, although rotation is possible, the desired position is nevertheless retained through the frictional forces occurring between the base and the base plate, since rotation can be effected only by the application of considerable force. In this connection it is particularly pointed out that the construction of the support table according to the invention is not restricted to the combination according to the invention, that is to say to those dental articulators in which the support table is situated on the upper frame part of the dental articulator, but can also be advantageously applied to conventional dental articulators. In view of this fact, separate protection is claimed for the forms of construction of the support table described herein, irrespective of the type of dental articulator concerned, that is to say whether the support table is disposed on the upper frame part or on the lower frame part.

In view of the fact that according to the present invention the support table for the front tooth guide pin is disposed on the upper frame part and the front tooth guide pin is disposed on the lower frame part, it has been found expedient to carry out the examinations in the articulator with the latter on its back, so that the upper frame part lies at the bottom. It has however been found that in this position the lower frame part could not, because of its construction, provide secure support. Another important feature of the invention therefore comprises the support device according to the invention, which is situated on the upper face of the upper frame part, roughly above the articulation sockets. The support device can form a unit with the upper frame part, that is to say the support device and the upper frame part are an integral casting, or else the support device may be attached to the upper frame part. The support device itself may have any desired shape, provided that it gives secure support and allows the articulation sockets to be turned to any desired position, the ideal arrangement enabling the articulation sockets to be turned through 360°. It has in addition been found advantageous to provide support in a position in which the support points extend below the articulation sockets. It is immaterial whether the support extends over the entire length of the support device or whether practically punctiform support is provided under the articulation sockets. A so-called "three-point" support has been found particularly practical in use. In this case a V-shaped bow is provided on the top portion of the upper frame part, with the side arms of the bow bent over in such a manner that they come to lie practically centrally above the articulation sockets when the articulator is lying on its back, so that they do not hinder the turning of the articulation sockets to any desired position. Instead of a bow it would of course also be possible to provide a trapezium-shaped support device, without the function of the support device being affected. The third point is formed by the fastening screw by which the support table is fastened on the upper frame part. The support device according to the invention also prevents the articulation sockets from being displaced, when the articulator is laid on its back, through overturning of the articulator or of the upper frame part. The support device according to the invention can of course also advantageously be fitted to the upper frame parts of conventional articulators, since in this case also secure support is provided for the upper frame parts when they are laid on their backs.

According to the invention it has also been found that it is more advantageous for the cross-strut interconnecting the two carrier pillars, on which are mounted the balls serving as articulation heads, together with pins, not to be disposed at the upper end of the carrier pillars, as described for example in the previously mentioned German Patent Specification No. 2,511,388, but to be disposed in the middle region of the carrier pillars, without the stability of the lower part or of the carrier pillars in relation to one another being endangered. In this way better visibility is obtained, and thus also better ability to observe the tooth movement in the model, since a better view is obtained of the tongue space between the jaws.

The invention is explained below with reference to FIGS. 1 to 8, which illustrate particularly preferred embodiments of the invention, without however restricting the invention thereto. Any details not mentioned in the description but visible in the drawings form an integral part of the disclosure of the present invention. The references shown in the drawings and in the appertaining parts of the description are repeated in the form of a list at the end of the description.

BRIEF DESCRIPTION OF THE DRAWINGS

FIGS. 2a to 2d are partial views showing a first modified embodiment of the support table of FIG. 1, and wherein:

FIG. 2a is a side elevational view of the modified support table, wherein it is oriented as if viewed from the opposite side of the dental articulator of FIG. 1, FIG. 2b is a sectional view taken along line 2b—2b of FIG. 2a, FIG. 2c is a top plan view of FIG. 2a, and FIG. 2d is a bottom plan view of FIG. 2a.

FIGS. 5a to 5c show only the base plate of FIGS. 3 and 4, wherein:

FIG. 5a is a sectional view similar to FIG. 4,

FIG. 5b is a top plan view of FIG. 5a, and

FIG. 5c is a bottom plan view of FIG. 5a.

FIGS. 6a to 6d show only the upper of the two table plate parts of FIGS. 3 and 4, wherein:

FIG. 6a is a sectional view similar to FIG. 4,

FIG. 6b is a side elevational view of the part shown in FIG. 6a,

FIG. 6c is a top plan view of FIG. 6a, and

FIG. 6d is a bottom plan view of FIG. 6a.

FIGS. 7a and 7b show only the lower of the two table plate parts of FIG. 3, wherein FIG. 7a is a top plan view thereof, and FIG. 7b is a sectional view taken along line 7b—7b of FIG. 7a.

DETAILED DESCRIPTION OF THE PREFERRED EMBODIMENT

Figure 1:
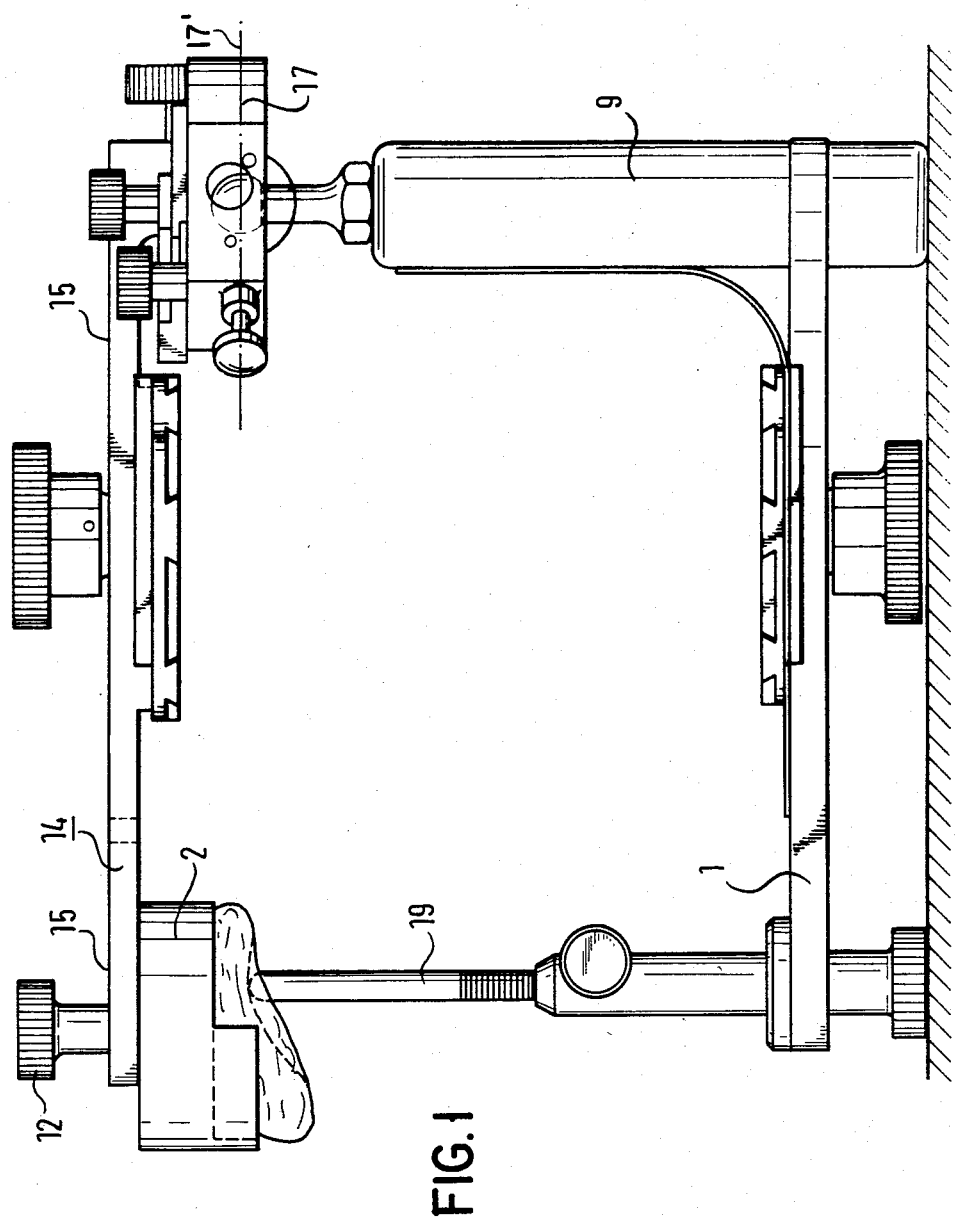
FIG. 1 is a side elevational view of a dental articulator according to the invention, showing a first embodiment of a support table thereon.

The dental articulator according to the present invention is depicted in FIG. 1 and includes a front tooth guide pin 19 mounted on a lower frame part 1. Articulation sockets 17 define a horizontal reference plane 17' corresponding to the jaw hinge or joint plane. A support table 2 is mounted on the upper frame part 14. A modified support table 2' is shown in greater detail in FIGS. 2a to 2d.

Figure 2A:
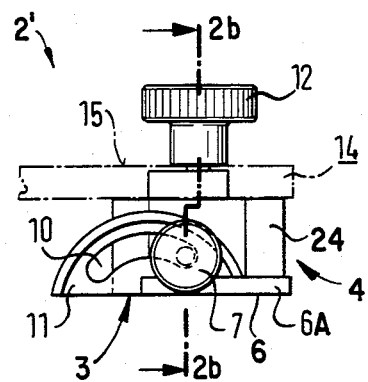
Figure 2B:
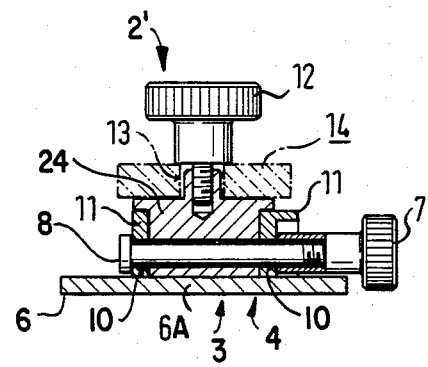
Figure 2C:
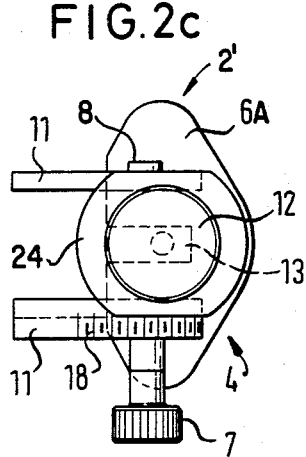
Figure 2D:
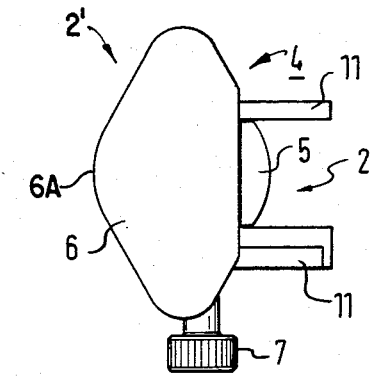

As shown in FIGS. 2a to 2d, support table 2' includes a table plate 4 having a plinth 24 provided with a region 5 which remains invariably in the horizontal position and a part 6A provided with a region 6 which is pivotable relative to region 5. A locking screw 7 is provided to lock pivotable region 6 of table plate 4 in the desired position. A locking pin 8 is disposed at the end of locking screw 7. Both locking screw 7 and locking pin 8 engage in slots 10 provided in pivoted discs 11 so that pivotable region 6 of table plate 4 is guided during pivoting movement. The support table 2' itself is fastened to the upper frame part 14 by means of a fastening screw 12, as best shown in FIGS. 2a and 2b. The support table 2' is guided in the upper frame part 14 by the guide slot 13. In order to read the pivoted position of region 6 of support table 2' at any given moment, a scale 18 is provided on the pivoted disc 11.

Figure 3:
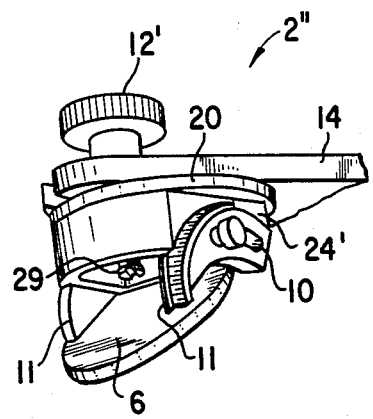
FIG. 3 is a perspective view, taken from below, off to the left side, of a second modified support table of FIG. 1.
Figure 4:
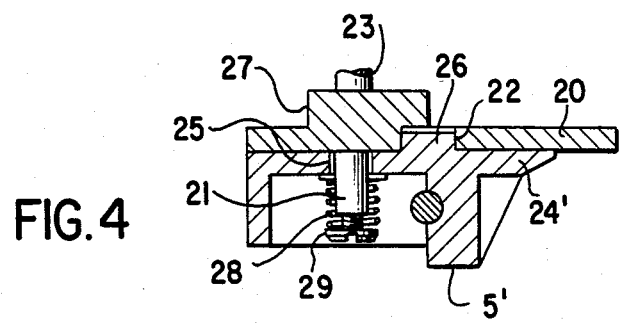
FIG. 4 is central sectional view through the support table of FIG. 3, including only the base plate and the upper of the two table plate parts.
Figure 5C:
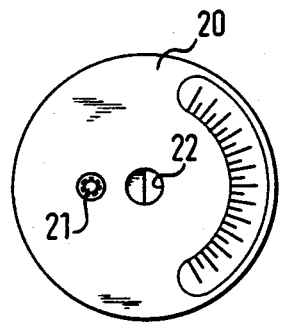
Figure 5B:
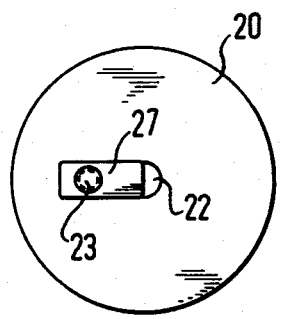
Figure 5A:
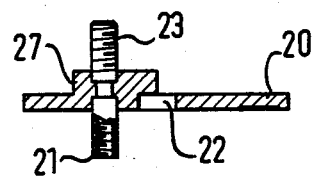
Figure 6A:
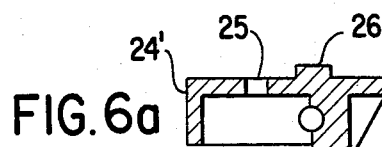
Figure 6B:
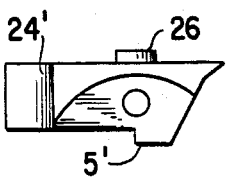
Figure 6D:
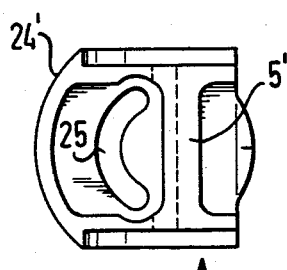
Figure 6C:
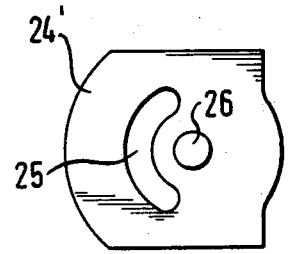

Depicted in FIGS. 5a, 5b and 5c, is a base plate 20 which is part of a further modified support table 2" depicted in FIGS. 3 and 4. A cylindrical cutout 22 is also provided in base plate 20 through which a pivot pin 26 (shown in FIGS. 4, 6a, 6b and 6c) extends. A screw stem 21 having an internal screw thread is also located in base plate 20.

Base plate 20 also includes a guide block 27. Guide block 27 is introduced into a corresponding rectangular slot 13 in the upper frame part 14. An externally threaded screw 23 projects from guide block 27 on which a locking nut 12', similar to locking nut 12 depicted in FIGS. 2a to 2d, is attached.

Depicted in FIGS. 3, 4, 6a, 6b, 6c and 6d is a plinth 24' which is one part of table plate 4'. Plinth 24' includes region 5' whose position does not vary as described above with respect to region 5 of FIGS. 2a, 2b, 2c, and 2d. Plinth 24' also includes a guide and pressure slot 25 through which, after assembly, the screw stem 21 of the base plate 20 projects for fastening by a screw and spring arrangement (as shown in FIG. 4 and described below).

The assembly of plinth 24' and base plate 20 is depicted in FIG. 4. As shown, the cylindrical pivot pin 26 of plinth 25 projects into cylindrical cutout 22 of base plate 20. Screw stem 21, joined to base plate 20, projects through the guide and pressure slot 25 provided in plinth 24'. A helical spring 28 is disposed over the screw stem 21. Spring 28 is compressed by a pressure screw 29 screwed into screw stem 21. In this manner, plinth 24' is pressed against the base plate 20 with a predetermined spring force.

Figure 7A:
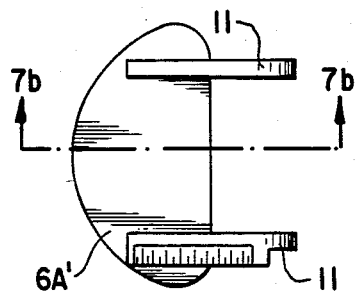
Figure 7B:
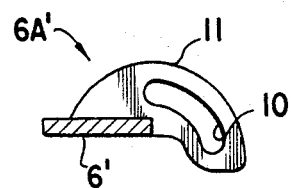

Depicted in FIGS. 7a and 7b is the other part of 6a' of table plate 4'. This part contains a region 6' similar to the region 6 described above. Also shown in greater detail are pivot discs 11' which were similarly described above.

The assembled support table 2" is depicted in FIG. 3 in perspective. Support table 2" is connected by the base plate 20 to the upper frame part 14 of the dental articulator.

Figure 8:
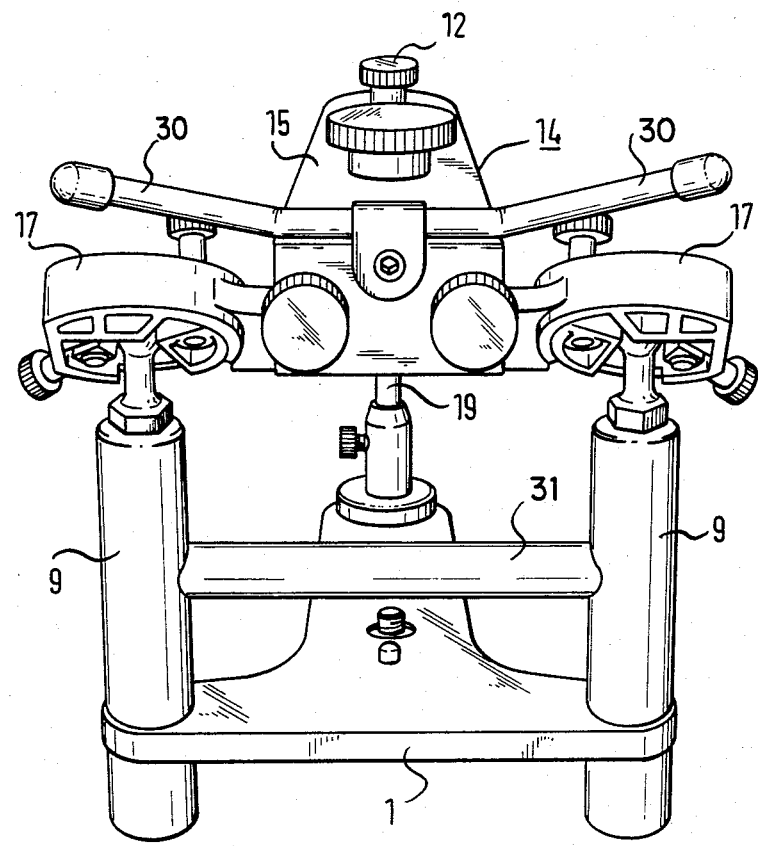
FIG. 8 is an end elevational view of a dental articulator similar to FIG. 2 except that the parts are slightly moved and a support device is included.

The dental articulator according to the present invention is depicted as well in FIG. 8. The support table 2' or 2" is disposed on the upper frame part 14 while the front tooth guide pin 19 is disposed on lower frame part 1. A support device 30 is mounted on the upper portion 15 of the upper frame part 14 as shown. Also clearly shown in this Figure is the middle position of cross strut 31 joining carrier pillars 9 together. The support table for this dental articulator is preferably the support table 2" depicted in FIG. 3.

List of References

1 Lower frame part
2 Support table
3 Plane of the support table 2
4 Table plate of the support table 2
5 Region of the table plate 4 which invariably remains in the horizontal position
6 Pivotable region of the table plate 4
7 Locking screw for locking the pivotable region 6 of the table plate 4
8 Cross-strut
9 Carrier pillars
10 Slots in the pivot discs 11
11 Pivot discs fastened to the pivotable region 6 of the table plate
12 Fastening screw
13 Locking pin
14 Upper frame part
15 Upper portion of the upper frame part 14
16 Support device
17 Articulation sockets
18 Scale
19 Front tooth guide pin (previously also called cutting tooth guide pin)
20 Base plate
21 Screw stem with internal screwthread
22 Cylindrical cutout for the cylindrical pivot pin 26
23 Externally threaded screw for the locking nut 12a (corresponds to the locking screw 12 in FIGS. 2a–2d)
24 Plinth with the region 5 of the table plate 4 which is invariable in position.
25 Guide and pressure slot
26 Cylindrical pivot pin
27 Guide block
28 Helical spring
29 Pressure screw

I claim:

1. A dental articulator comprising:
a lower frame part with a generally horizontal holding device for a mounting plate for a lower jaw model;
a vertical frame part which is fastened to the lower frame part and which has two articulation heads;
an upper frame part with a generally horizontal holding device for a mounting plate for an upper jaw model and also with two radially rotatable articulation sockets which engage a respective said articulation head and which together form a horizontal pivot axis for said upper frame part, said horizontal pivot axis corresponding to the jaw joint and defining a horizontal reference plane parallel to both said holding devices;
a vertically adjustable front tooth guide pin disposed on the lower frame part;
a support table disposed on the upper frame part and divided into two regions, one region being a planar portion which provides a central support region for the point of impact of the front tooth guide pin before commencement of the excursions of the guide pin and which remains invariably in the horizontal position in the reference plane before commencement of the excursions, the other region being pivotable forwards and downwards at the front relative to the one region such that the points of impact of the excursions of the guide pin take place on the other region.

2. An articulator as claimed in claim 1, wherein the support table is rotatably connected, in the manner of a turntable, by a plinth to a base plate which is secured to the dental articulator by a locking nut.

3. An articulator as claimed in claims 1 or 2 wherein a cross-strut is connected between two carrier pillars projecting from the lower frame part in the middle region instead of in the upper region.

* * * * *